United States Patent [19]

Kakimoto

[11] Patent Number: 4,863,381

[45] Date of Patent: Sep. 5, 1989

[54] DENTAL HANDPIECE

[75] Inventor: Masakazu Kakimoto, Aichi, Japan

[73] Assignee: Ushio Kogyo Co., Ltd., Aichi, Japan

[21] Appl. No.: 122,854

[22] Filed: Nov. 17, 1987

[30] Foreign Application Priority Data

Mar. 6, 1987 [JP] Japan .................................. 62-52349

[51] Int. Cl.⁴ .................................................. A61C 1/14
[52] U.S. Cl. ................................................... 433/129
[58] Field of Search .......................... 433/129, 128, 127

[56] References Cited

U.S. PATENT DOCUMENTS

| 222,181 | 12/1879 | Donaldson | 433/127 |
| 3,994,070 | 11/1976 | Loge | 433/127 |

FOREIGN PATENT DOCUMENTS

| 0135327 | 5/1985 | European Pat. Off. | 433/129 |
| 2718750 | 11/1978 | Fed. Rep. of Germany | 433/127 |
| 692753 | 6/1953 | United Kingdom | 433/128 |

*Primary Examiner*—John J. Wilson
*Attorney, Agent, or Firm*—Sandler & Greenblum

[57] ABSTRACT

The improved dental handpiece comprises an operating sleeve slidably mounted on an outer circumference of the rotor shaft, said operating sleeve being formed with a flange, a spring for normally biasing the operating sleeve frontwardly, an operation collar threadedly engaged with an outer circumference of the outer cylinder, a pusher ring interposed between an inner surface of the operation collar and a front surface of the flange of the operating sleeve, a cylindrical portion formed at a front portion of the rotor shaft for receiving the main shaft of the working tool, a plurality of key holes formed through a wall of the cylindrical portion at a position opposed to an inner surface of the operating sleeve in such a manner as to be arranged at equal intervals on the same circumference, each of said key holes having a segment-like shape in cross section, a plurality of chuck keys engaged in the key holes, each of said chuck keys having a shape corresponding to the shape of each key hole in such a manner that an upper surface of each chuck key is formed with a frontwardly diverged inclined portion projectable from the outer circumference of the cylindrical portion of the rotor shaft.

9 Claims, 2 Drawing Sheets

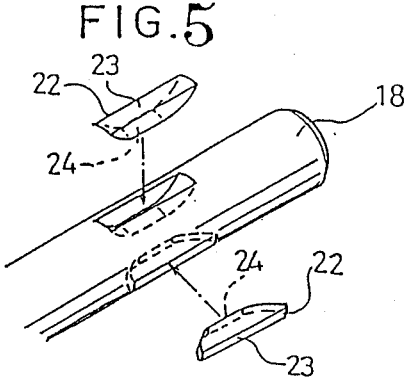
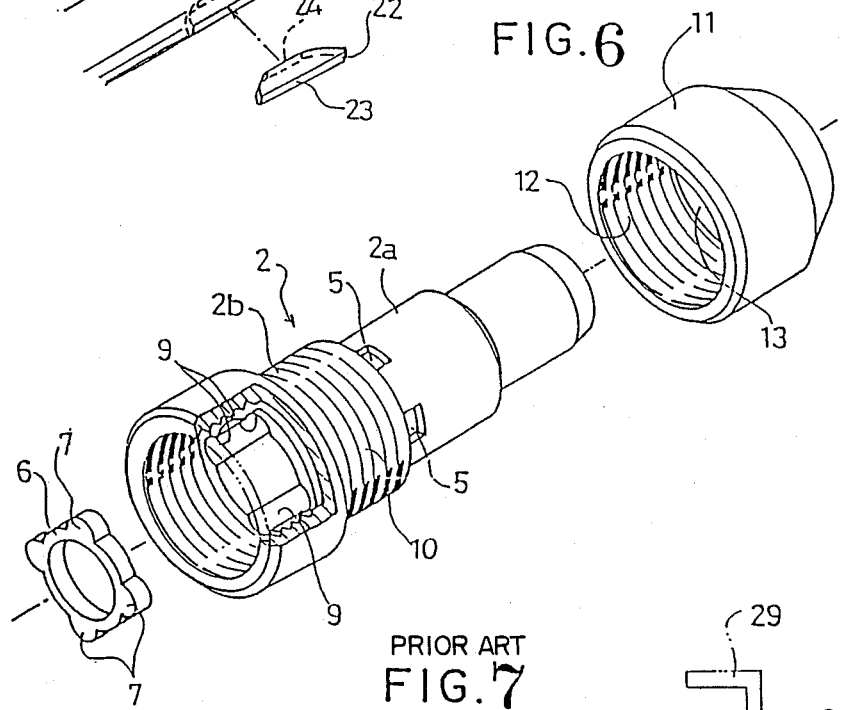
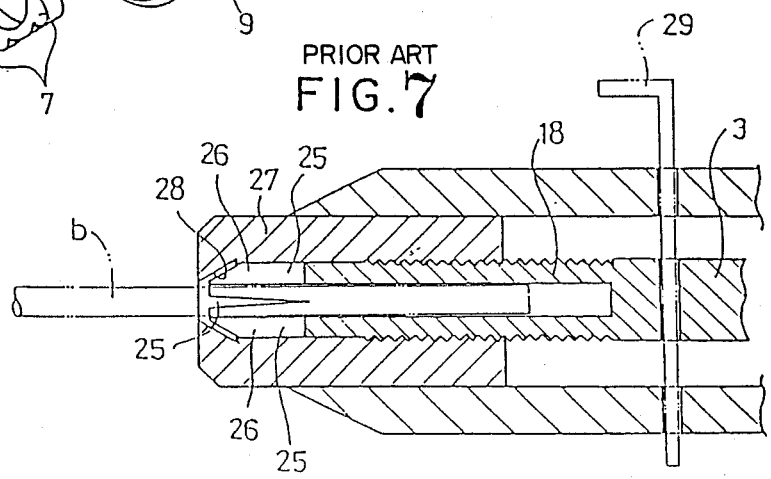

4,863,381

DENTAL HANDPIECE

BACKGROUND OF THE INVENTION

The present invention relates to a dental handpiece, and more particularly to a handpiece to be employed for dental treatment or techniques.

Generally, the dental handpiece is used with its associated working tool or instrument such as a grinder, polisher and drilling tool exchanged according to the purpose of use. The dental handpiece includes a casing having an air motor or an electric motor therein, an outer cylinder projecting from a front end of the casing, a rotor shaft of the motor extending in the outer cylinder, and a main shaft of the working tool detachably inserted into a front portion of the rotor shaft.

From a safety point of view in the handpiece, the working tool must be reliably assembled with the rotor shaft, and it must be also easily assembled and disassembled manually.

Referring to FIG. 7 showing a conventional dental handpiece, a rotor shaft 3 is formed at its front end portion with a cylindrical portion 18 for inserting a main shaft b of a working tool therein. The cylindrical portion 18 is formed at its front end portion with slits 25 to form holding portions 26. A nut 27 is threadedly engaged with an outer circumference of the cylindrical portion 18. When the nut 27 is firmly tightened, the holding portions 26 are pressed radially inwardly by an inner peripheral surface 28 formed at the front end of the nut 27. As a result, an inner surface of the holding portions 26 is brought into abutment against the main shaft b, thus fixing the main shaft.

In the conventional handpiece as mentioned above, as the rotor shaft 3 is idly rotated, it is necessary to insert a pin 29 so as to lock the idling of the rotor shaft 3 upon tightening the nut 27. Further, as the main shaft b of the working tool is very small in diameter, the diameters of the rotor shaft 3 and the nut 27 are also small. Accordingly, a sufficient holding force cannot be obtained by manually rotating the nut 27, and it is therefore necessary to use a spanner (not shown) for firmly tightening the nut 27. Thus, it is hard to easily exchange the working tool during the operation.

SUMMARY OF THE INVENTION

It is an object of the present invention to provide a dental handpiece which permits a working tool to be easily mounted and demounted.

It is another object of the present invention to provide a dental handpiece which permits the working tool to be reliably and safely engaged with a rotor shaft.

According to the present invention, there is provided in a dental handpiece including a casing having a motor therein, an outer cylinder projecting from a front end of the casing, a rotor shaft of the motor extending in the outer cylinder, and a main shaft of a working tool detachably inserted into a front portion of the rotor shaft; the improvement comprising an operating sleeve slidably mounted on an outer circumference of the rotor shaft, said operating sleeve being formed with a flange, a spring for normally biasing the operating sleeve frontwardly, an operation collar threadedly engaged with an outer circumference of the outer cylinder, a pusher ring interposed between an inner surface of the operation collar and a front surface of the flange of the operating sleeve, a cylindrical portion formed at a front portion of the rotor shaft for receiving the main shaft of the working tool, a plurality of key holes formed through a wall of the cylindrical portion at a position opposed to an inner surface of the operating sleeve in such a manner as to be arranged at equal intervals on the same circumference, each of said key holes having a segment-like shape in cross section, a plurality of chuck keys engaged in the key holes, each of said chuck keys having a shape corresponding to the shape of each key hole in such a manner that an upper surface of each chuck key is formed with a frontwardly diverged inclined portion projectable from the outer circumference of the cylindrical portion of the rotor shaft.

In operation, when the operation collar is manually screwed frontwardly, the operating sleeve slidably mounted on the outer circumference of the rotor shaft is biased frontwardly by the spring. As a result, the inner surface of the operating sleeve is brought into abutment against the frontwardly diverging inclined portion of the upper surface of the chuck key. Accordingly, the chuck key is pressed downwardly by the wedge action of both the surfaces, and the lower surface of the chuck key is therefore strongly pressed on the outer circumference of the main shaft of the working tool inserted into the cylindrical portion of the rotor shaft. Thus, the main shaft is fixedly connected with the rotor shaft in coaxial relationship therewith.

In contrast, when the operation collar is manually screwed rearwardly, the inner surface of the collar moves rearwardly the operating sleeve through the pusher ring and the flange against the biasing force of the spring. As a result, the abutment of the inner surface of the operating sleeve against the upper surface of the chuck key is released, and the pressing force of the lower surface of the chuck key as applied to the outer circumference of the main shaft is therefore removed. Thus, the main shaft may be drawn from the rotor shaft.

As described above, the engagement and disengagement between the main shaft of the working tool and the rotor shaft may be effected by axially sliding the operating sleeve along the outer circumference of the rotor shaft without applying a torque to the rotor shaft. Therefore, it is not necessary to provide an idling stopper of the rotor shaft. Furthermore, as the sliding action of the operating sleeve is effected by screwing the large-diameter operation collar threadedly engaged with the outer circumference of the outer cylinder, the engagement and disengagement of the main shaft may be effected by a manual operation with a light force. Accordingly, it is possible to provide a handpiece with good operability without the need of any tools such as a rotor shaft idling stopper pin and a spanner.

Moreover, as the operating sleeve is biased by the spring frontwardly (in the tightening direction), it functions to gradually further strongly hold the main shaft of the working tool owing to the vibration and impact created during the operation, thus improving the safety in use.

Other objects and features of the invention will be more fully understood from the following detailed description and appended claims when taken with the accompanying drawings.

BRIEF DESCRIPTION OF THE DRAWINGS

FIG. 5 is an exploded perspective view of the chuck keys and the front end portion of the cylindrical portion of the rotor shaft;

FIG. 6 is an exploded perspective view of the outer cylinder, the pusher ring and the operation collar; and FIG. 7 is an enlarged sectional view of the essential part of the conventional handpiece.

DETAILED DESCRIPTION OF THE PREFERRED EMBODIMENT

Figure 1:
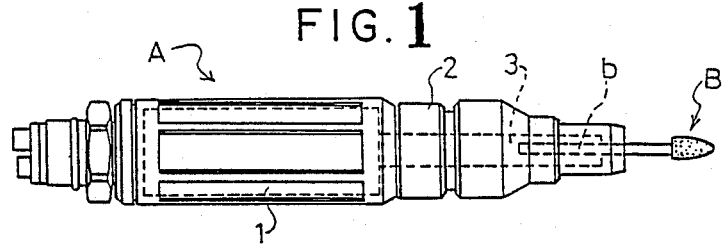
FIG. 1 is a side view of a dental handpiece of a preferred embodiment according to the present invention.
Figure 2:
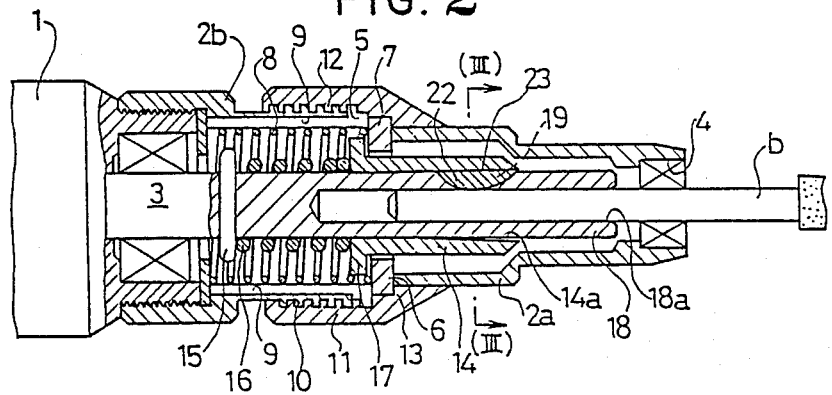
FIG. 2 is an enlarged sectional view of the essential part in FIG. 1 under the mounted condition of the working tool.
Figure 3:
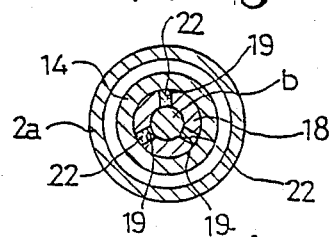
FIG. 3 is a cross section taken along the line III—III in FIG. 2.

Referring to FIGS. 1 to 6, a dental handpiece A includes a casing 1 having an air motor or an electric motor therein, an outer cylinder 2 projecting from a front end of the casing 1, a rotor shaft 3 of the motor extending in the outer cylinder 2, and a main shaft b of a working tool B detachably inserted into a front portion of the rotor shaft 3.

The outer cylinder 2 is a cylinder surrounding the rotor shaft 3 adapted to be rotated and having a desired length. A rear end of the outer cylinder 2 is releaseably threadedly engaged with the front end of the casing 1. A front end opening 4 of the outer cylinder 2 is located at a position just front of a front end of the rotor shaft 3. The outer cylinder 2 is generally formed by a front half section 2a between the front end and an intermediate portion and a rear half section 2b between the intermediate portion and the rear end.

The front half section 2a is a cylinder having a desired length and diameter. The main shaft b of the working tool B is inserted from the front end opening 4 into the front end of the rotor shaft 3. The rear end of the front half section 2a is integrally coaxially connected to the rear half section 2b, and is formed along the circumference with four apertures 5 equally spaced to each other. The apertures 5 are formed through a wall of the front half section 2a, and has a desired axial length.

A pusher ring 6 is inserted into the rear end of the front half section 2a. The pusher ring 6 is an annular member having an outer diameter slightly smaller than an inner diameter of the front half section 2a and having a desired inner diameter. The pusher ring 6 is integrally formed at its outer circumference with four projections 7 opposed to the apertures 5 of the front half section 2a.

The projections 7 have a desired height from the outer circumference of the pusher ring 6, and a part of each projection 7 from an intermediate position to a top end thereof is projected from each aperture 5. The pusher ring 6 is adapted to be slid at the rear end portion of the front half section 2a within the axial length of the apertures 5.

A return spring 8 is installed on the rear side of the pusher ring 6 to normally bias the same frontwardly. Therefore, the front surface of the projections 7 is normally abutted against the front end surface of the apertures 5.

The rear half section 2b is a cylinder having an inner diameter substantially the same as the outer diameter of the front half section 2a and having a desired length. The front end of the rear half section 2b is integrally connected to the rear end of the front half section 2a, while the rear end of the rear half section 2b is threadedly engaged with the front end of the casing 1. The rear half section 2b is formed at its inner circumference with four guide channels 9 and at its outer circumference with a threaded portion 10.

The guide channels 9 are opposed at their front end to the apertures 5 of the front half section 2a, and extend from the front end of the rear half section 2b to the rear end thereof. Each of the guide channels 9 has a depth such that the projections 7 of the pusher ring 6 can be slid therealong, and is communicated at its front end with the apertures 5.

That is, upon installing the pusher ring 6 from the rear end of the rear half section 2b to the rear end of the front half section 2a, the guide channels 9 serve to guide the projections 7 of the pusher ring 6 toward the apertures 5.

The threaded portion 10 of the rear half section 2a has a desired axial length, and is engaged with an operation collar 11.

The operation collar 11 is a cylinder having a desired length and outer diameter, and is formed at its inner circumference with female threads 12 movably engaging the threaded portion 10. The operation collar 11 is further formed at its front end of the inner circumference with an engagement projecting portion 13 engaging the front surface of the projections 7.

Figure 4:
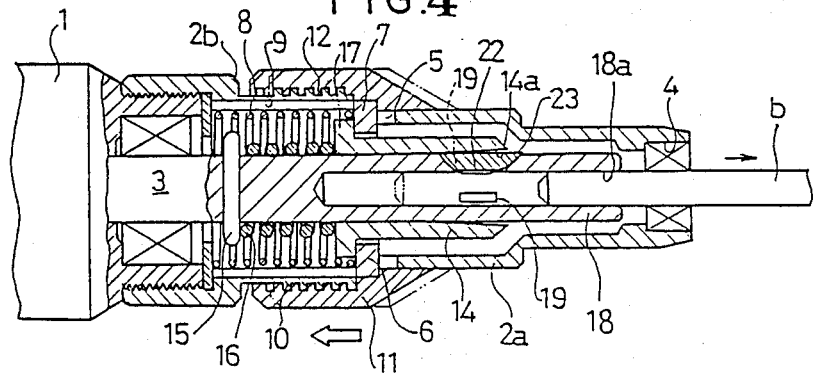
FIG. 4 is a view similar to FIG. 2 upon disengaging the working tool.

When the operation collar 11 is rearwardly screwed in a direction shown by an arrow in FIG. 4, the engagement projecting portion 13 of the collar 11 rearwardly moves the projections 7 of the pusher ring 6 to the rear end of the apertures 5. In contrast, when the operation collar 11 is frontwardly screwed, the pusher ring 6 is returned to the front end of the apertures 5 by the return spring 8.

The rotor shaft 3 having a desired length extends from the front end of the casing 1 in coaxial relationship with the outer cylinder 2. The rotor shaft 3 is integrally connected at its base (rear end) to a rotor (not shown) provided in the casing 1, and is adapted to rotate with the rotor to drive the main shaft b of the working tool B.

An operating sleeve 14 is mounted on the outer circumference of the rotor shaft 3 in such a manner as to be slidable in the axial direction. A pin 15 is inserted through the rotor shaft 3 in perpendicular relationship thereto at a desired rear position of the operating sleeve 14. A spring 16 is interposed between the operating sleeve 14 and the pin 15.

The operating sleeve 14 has an inner diameter slightly larger than the outer diameter of the rotor shaft 3 and has an outer diameter slightly smaller than the inner diameter of the pusher ring 6. The operating sleeve 14 is formed at its inner peripheral end portion 14a with a divergingly inclined surface, and is further formed at the rear end with an annular flange 17, a front surface of which abuts against the rear surface of the pusher ring 6.

The spring 16 is a compression spring slidably mounted on the outer circumference of the rotor shaft 3. The spring 16 abuts at its front end against the rear end of the flange 17 and abuts at its rear end against the front end of the pin 15, thus normally biasing the operating sleeve 14 frontwardly.

The rotor shaft 3 is formed at its front portion with a cylindrical portion 18. The cylindrical portion 18 has a bore extending from the front end to an intermediate position of the rotor shaft 3. The diameter of the bore is about 2.4–2.5 mm which permits the main shaft b of the working tool B to be slidably inserted. The cylindrical portion 18 is formed at its front end with an insert opening 18a for inserting the main shaft b therefrom. A plurality of key holes 19 are formed through the wall of the cylindrical portion 18 in such a manner as to be arranged at equal intervals on the same circumference.

Each of the key holes 19 has a rectangular shape in plan and a segment-like shape in cross section. Namely, each key hole 19 has an outer opening 20 on the outer wall surface of the cylindrical portion 18 and an inner opening 21 on the inner wall surface thereof. The outer opening 20 has an axially elongated rectangular shape.

A plurality of chuck keys 22 are engaged in the key holes 19. Each of the chuck keys 22 has a hexahedral shape adapted to each key hole 19. An upper surface 23 of each chuck key 22 is an inclined surface frontwardly diverged, and the front end portion of the upper surface 23 is slightly projected from the outer opening 20 of the key hole 19. Thus, the chuck keys 22 are swingable longitudinally in the key holes 19.

When the inner peripheral end portion 14a of the operating sleeve 14 biased frontwardly by the spring 16 is pressed on the upper surface 23 of each chuck key 22, the chuck key 22 is swung to project a rear end of its lower surface 24 from the inner opening 21 of the key hole 19. As a result, the lower surface 24 of each chuck key 22 comes into press contact with the outer circumference of the main shaft b of the working tool B inserted into the cylindrical portion 18. At the same time, the swing motion of the chuck keys 22 is locked by the operating sleeve 14.

In contrast, when the operation collar 11 is rearwardly screwed to retract the pusher ring 6 and thereby axially retract the operating sleeve 14 through the flange 17 against the spring 16, the inner peripheral end portion 14a of the operating sleeve 14 is moved away from the upper surface 23 of the chuck key 22 to thereby release the press contact between the lower surface 24 of the chuck key 22 and the main shaft b. Thus, the main shaft b may be drawn from the rotor shaft 3.

As described above, since the inner peripheral end portion 14a of the operating sleeve 14 is an inclined surface frontwardly diverged, the engagement and disengagement between the inner peripheral end portion 14a and the upper surface 23 of the chuck key 22 may be effected by slightly sliding the operating sleeve 14. Accordingly, a screwing range of the operation collar 11 may be reduced, thereby making the exchanging operation of the working tool B more easy.

While the invention has been described with reference to a specific embodiment, the description is illustrative and is not to be construed as limiting the scope of the invention. Various modifications and changes may occur to those skilled in the art without departing from the spirit and scope of the invention as defined by the appended claims.

What is claimed is:

1. A dental handpiece comprising
a casing provided with a motor;
an outer cylinder projecting from a front end of said casing;
a rotor shaft extending from said motor in said outer cylinder;
a main shaft of a working tool detachably inserted into a front portion of said rotor shaft;
an operating sleeve slidably mounted on an outer circumference of side rotor shaft, said operating sleeve being formed with a flange;
a spring for normally biasing said operating sleeve frontwardly;
an operation collar threadedly engaged with an outer circumference of said outer cylinder;
a pusher ring interposed between an inner surface of said operation collar and a front surface of said flange of said operating sleeve;
a cylindrical portion formed at a front portion of said rotor shaft for receiving said main shaft of said working tool;
a plurality of key holes formed through a wall of said cylindrical portion at a position opposed to an inner surface of said operating sleeve in such a manner as to be arranged at equal intervals on a common circumference, wherein each of said key holes have a segment-like shape in cross section;
a plurality of chuck keys engaged in said key holes, wherein each of said chuck keys have a shape corresponding to the shape of each key hole in such a manner that an upper surface of said each of said chuck keys is formed with a frontwardly diverged inclined portion projectable from the outer circumference of said cylindrical portion of said rotor shaft.

2. The dental handpiece as defined in claim 1 further comprising a plurality of apertures each having a predetermined axial length formed at a rear end of a front half section of said outer cylinder at circumferentially equal intervals.

3. The dental handpiece as defined in claim 2 further comprising a plurality of projections formed on an outer circumference of said pusher ring in opposed relationship to said apertures, said projections being axially slidable within said predetermined axial length of said apertures.

4. The dental handpiece as defined in claim 3 further comprising a return spring provided on a rear side of said pusher ring for normally biasing said pusher ring and abutting a front surface of said projections against a front end of said apertures.

5. The dental handpiece as defined in claim 1 further comprising a pin inserted through said rotor shaft in perpendicular relationship thereto at a desired rear position of said operating sleeve.

6. The dental handpiece as defined in claim 5, wherein said spring comprises a compression spring slidably mounted on the outer circumference of said rotor shaft between a rear surface of said flange and a front end of said pin.

7. The dental handpiece as defined in claim 1, wherein said operating sleeve is formed at its inner peripheral end portion with an inclined surface frontwardly diverged.

8. The dental handpiece as defined in claim 1, wherein said chuck keys are swingable longitudinally in said key holes.

9. A dental handpiece comprising:
a casing provided with a motor;
an outer cylinder projecting from a front end of said casing;
a plurality of apertures each having a predetermined axial length formed at a rear end of a front half section of said outer cylinder at circumferentially equal intervals;

a rotor shaft of said motor extending in said outer cylinder, and a main shaft of a working tool detachably inserted into a front portion of said rotor shaft;

an operating sleeve slidably mounted on an outer circumference of said rotor shaft, said operating sleeve being formed with a flange;

a spring for normally biasing said operating sleeve frontwardly;

an operation collar threadedly engaged with an outer circumference of said outer cylinder;

a pusher ring interposed between an inner surface of said operation collar and a front surface of said flange of said operating sleeve;

a plurality of projections formed on an outer circumference of said pusher ring in opposed relationship to said apertures, said projections being axially slidable within said predetermined axial length of said apertures;

a plurality of guide channels formed on an inner circumference of a rear half section of said outer cylinder at a position opposed to said apertures, said guide channels having a predetermined axial length and a depth such that said projections are slidable along said guide channels;

a cylindrical portion formed at a front portion of said rotor shaft for receiving said main shaft of said working tool;

a plurality of key holes formed through a wall of said cylindrical portion at a position opposed to an inner surface of said operating sleeve in such a manner as to be arranged at equal intervals on the same circumference, each of said key holes having a segment-like shape in cross section;

a plurality of chuck keys engaged in said key holes, each of said chuck keys having a shape corresponding to the shape of each key hole in such a manner that an upper surface of said each chuck key is formed with a frontwardly diverged inclined portion projectable from the outer circumference of said cylindrical portion of said rotor shaft.

* * * * *